United States Patent
Li et al.

(10) Patent No.: US 9,573,934 B2
(45) Date of Patent: *Feb. 21, 2017

(54) METHODS AND COMPOSITIONS FOR THE SYNTHESIS OF MULTIMERIZING AGENTS

(71) Applicant: ARIAD Pharmaceuticals, Inc., Cambridge, MA (US)

(72) Inventors: Feng Li, Winchester, MA (US); Yihan Wang, Newton, MA (US)

(73) Assignee: ARIAD Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/607,831

(22) Filed: Jan. 28, 2015

(65) Prior Publication Data

US 2015/0148543 A1 May 28, 2015

Related U.S. Application Data

(63) Continuation of application No. 13/981,051, filed as application No. PCT/US2012/022642 on Jan. 26, 2012, now Pat. No. 9,024,028.

(60) Provisional application No. 61/436,430, filed on Jan. 26, 2011.

(51) Int. Cl.

| | |
|---|---|
| *C07D 211/60* | (2006.01) |
| *C07C 51/06* | (2006.01) |
| *C07C 209/08* | (2006.01) |
| *C07C 231/02* | (2006.01) |
| *C07C 235/34* | (2006.01) |
| *C07D 205/04* | (2006.01) |
| *C07D 319/06* | (2006.01) |
| *C07D 401/12* | (2006.01) |
| *C07D 319/04* | (2006.01) |
| *C07B 53/00* | (2006.01) |
| *C07C 209/62* | (2006.01) |
| *C07C 209/74* | (2006.01) |
| *C07C 231/18* | (2006.01) |

(52) U.S. Cl.
CPC ............. *C07D 401/12* (2013.01); *C07B 53/00* (2013.01); *C07C 51/06* (2013.01); *C07C 209/08* (2013.01); *C07C 209/62* (2013.01); *C07C 209/74* (2013.01); *C07C 231/02* (2013.01); *C07C 231/18* (2013.01); *C07C 235/34* (2013.01); *C07D 205/04* (2013.01); *C07D 211/60* (2013.01); *C07D 319/04* (2013.01); *C07D 319/06* (2013.01); *C07B 2200/07* (2013.01)

(58) Field of Classification Search
None
See application file for complete search history.

(56) References Cited

U.S. PATENT DOCUMENTS

| | | |
|---|---|---|
| 5,580,993 A | 12/1996 | Villa et al. |
| 6,150,527 A | 11/2000 | Holt et al. |
| 6,417,403 B1 | 7/2002 | Roh et al. |

OTHER PUBLICATIONS

Amara et al., "A Versatile Synthetic Dimerizer for the Regulation of Protein-Protein Interactions", Proc. Natl. Acad. Sci., 1997, pp. 10618-10623, vol. 94.
Anderson, Jr et al., Azetidines, IV, The Reaction of 1,1-Dimethyl-, 1-Benzyl-1-methyl-, and 1,1-Dibenzyl-3,3-dimethylazetidinium Salts with Alkali Metal Amides in Liquid Ammonia, The Journal of Organic Chemistry, 1968, pp. 3046-3050, vol. 33(8).
Annenkov et al., "Synthesis of Biomimetic Polyamines", ARKIVOC 2009, (xiii), pp. 116-130.
Clackson et al., "Redesigning an FKBP-ligand Interface to Generate Chemical Dimerizers with Novel Specificity", Proc. Natl. Acad. Sci., 1998, pp. 10437-10442, vol. 95.
Keenan et al., "Synthesis and Activity of Bivalent FKBP12 Ligands for the Regulated Dimerization of Proteins", Bioorganic & Medicinal Chemistry,1998, pp. 1309-1335, vol. 6.
Yang et al., "Investigating Protein-Ligand Interactions with a Mutant FKBP Possessing a Designed Specificity Pocket", 2000, pp. 1135-1142, vol. 43.
Int'l Search Report & Written Opinion dated Jul. 13, 2012 for PCT/US2012/022642 filed Jan. 26, 2012.

*Primary Examiner* — Timothy R Rozof
(74) *Attorney, Agent, or Firm* — Henry H. Gu

(57) ABSTRACT

The invention features methods and compositions for the synthesis of multimerizing agents.

20 Claims, No Drawings

METHODS AND COMPOSITIONS FOR THE SYNTHESIS OF MULTIMERIZING AGENTS

CROSS-REFERENCE TO RELATED APPLICATIONS

The present application is a continuation of U.S. Ser. No. 13/981,051, filed on Jan. 2, 2014, which claims priority under 35 U.S.C. §371 to International Application No. PCT/US2012/022642, filed Jan. 26, 2012, which claims priority to 35 U.S.C. §119(e) to U.S. Provisional Patent Application No. 61/436,430, filed Jan. 26, 2011. The entire contents of each of the above-referenced applications are hereby incorporated by reference in their entirety.

BACKGROUND OF THE INVENTION

The present invention relates to methods and compositions for the synthesis of multimerizing agents.

AP20187 is a small organic compound [CAS Registry No. 195514-80-8, molecular weight 1482.75] that induces controlled biological processes within cells having appropriate genetic alterations. AP20187 and related compounds provide a means for regulating genetically modified cells on the principle that intracellular signaling mechanisms can be regulated by specific protein-protein interactions. By selecting protein interactions that produce a desired cellular response and engineering those proteins to interact only in the presence of a small-molecule multimerizing agent, such as AP20187, it is possible to bring complex biological processes under direct control. For example, AP20187 can be used to regulate the production of therapeutic proteins and to control signal transduction in genetically altered cells to control cell death, proliferation, immune function, etc. The broad utility of AP20187 and other multimerizers has led to a significant body of scientific publications involving a range of biological contexts.

AP20187 includes multiple stereocenters. The configuration at each of the stereocenters has been found to be important to the biological activity of the compound. That structural complexity and chirality is also an important consideration in the production of the compounds. While methods and materials for the synthesis of AP20187, and related compounds, are disclosed in U.S. Pat. No. 6,150,527, new methods and intermediates which lend themselves to greater product purity and to greater overall efficiency, convenience, economics and/or scalability are particularly desirable.

SUMMARY OF THE INVENTION

The invention features methods and compositions for the synthesis of multimerizing agents.

The invention features the compound:

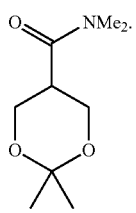

The invention features the compound:

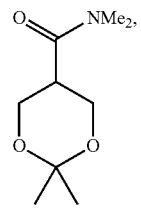

or a salt thereof.

The invention features the quaternary salt of 3-bromo-2-bromomethyl-N,N-dimethylpropylamine in solid form and described by the formula:

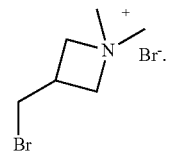

The invention also features the solid crystalline quaternary salt form of 3-bromo-2-bromomethyl-N,N-dimethylpropylamine described by the formula:

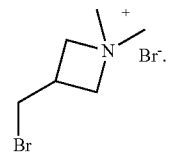

The invention features the compound AP22895 [CAS Registry No. 247118-51-0], having the formula:

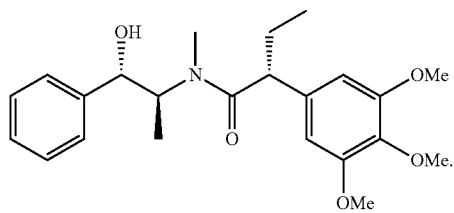 [SMILES: CC[C@@H](C(=O)N(C)[C@@H](C)[C@@H](O)c1ccccc1)c1cc(OC)c(OC)c(OC)c1]

The invention features a method for the chiral synthesis of the compound, AP17360, the method including: (a) reacting the compound AP22895 with ethyl iodide in the presence of a base to form compound X:

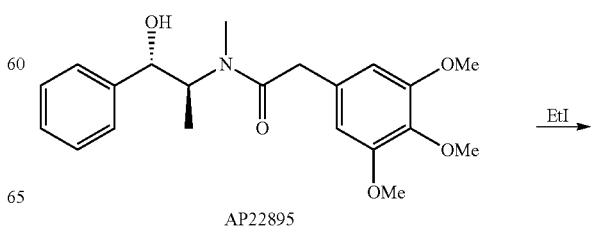

AP22895

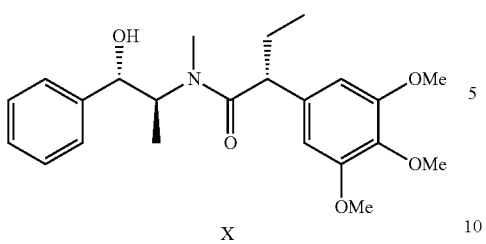

and (b) cleaving the compound X under acidic conditions to produce AP17360:

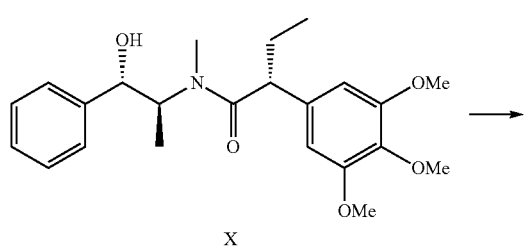

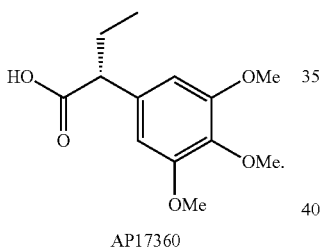

In particular embodiments, the base is lithium bis(trimethylsilyl)amide.

The invention features a method for producing dimethyl amide 3 by treating the corresponding ethyl ester with dimethylamine in the presence of base:

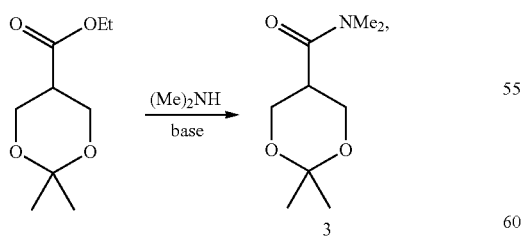

to form the desired dimethyl amide.

The invention features a method for producing compound 4 by providing the corresponding amide 3 and treating it with a reducing agent to produce compound 4:

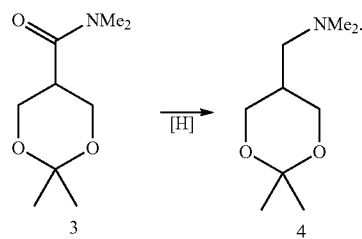

In certain embodiments, the reducing agent is LiAlH$_4$.

The invention features a method for producing 2-N,N-dimethylaminomethyl-1,3-diaminopropane (compound 6), the method including:

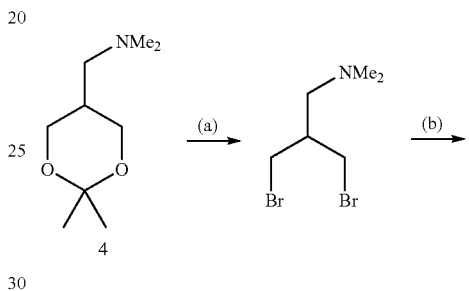

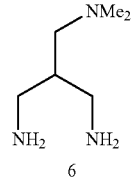

(a) reacting compound 4 with HBr to form 3-bromo-2-bromomethyl-N,N-dimethylpropylamine; and
(b) reacting the 3-bromo-2-bromomethyl-N,N-dimethylpropylamine with diformylamine to produce 2-N,N-dimethylaminomethyl-1,3-diaminopropane.

The invention features a method for producing 2-N,N-dimethylaminomethyl-1,3-diaminopropane (compound 6), the method including providing the quaternary salt:

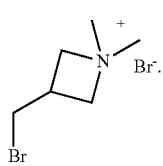

and reacting it with diformylamine to produce 2-N,N-dimethylaminomethyl-1,3-diaminopropane.

The invention features a method for producing AP20793:

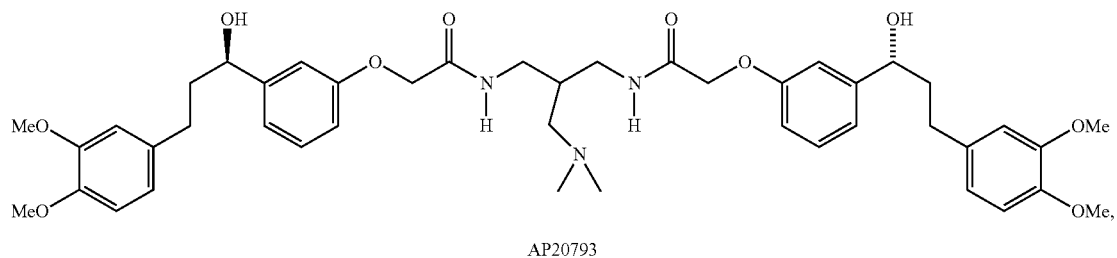 [SMILES: COc1ccc(CC[C@@H](O)c2cccc(OCC(=O)NCC(CNC(=O)COc3cccc([C@H](O)CCc4ccc(OC)c(OC)c4)c3)CN(C)C)c2)cc1OC]

AP20793 the method including: (a) dissolving a composition including the carboxylic acid, AP20792, of the formula:

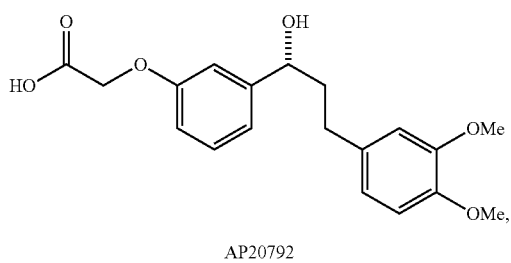 [SMILES: COc1ccc(CC[C@@H](O)c2cccc(OCC(=O)O)c2)cc1OC]

AP20792 in a solvent; (b) treating the resulting solution with a carboxyl activating agent to form activated AP20792; and (c) reacting the activated AP20792 with a composition including 2-N,N-dimethylaminomethyl-1,3-diaminopropane to form a mixture including AP20793. In some embodiments, the method further includes the step of producing 2-N,N-dimethylaminomethyl-1,3-diaminopropane from a quaternary salt as described herein, or from compound 4 as described herein.

The invention features a method for producing AP20187, having the formula:

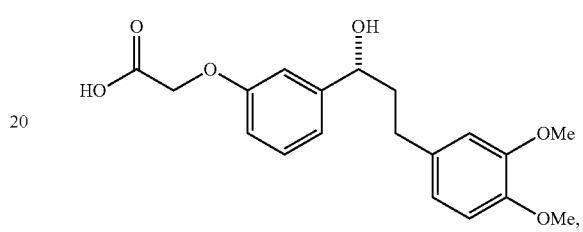

to yield AP20187.

The invention features a method for producing AP20187 by: (a) coupling 2-N,N-dimethylaminomethyl-1,3-diaminopropane with AP20792 to produce the dimeric alcohol, AP20793; and (b) coupling the AP20793 so produced with AP17362 to yield AP20187. In particular embodiments, the method further includes the step of producing AP17362 by coupling AP17360 with methyl-L-pipecolic acid, or a salt thereof.

The invention features a method for producing AP20187 by: (a) reacting 3-bromo-2-bromomethyl-N,N-dimethylpropylamine or the quaternary salt thereof with diformylamine to produce 2-N,N-dimethylaminomethyl-1,3-diaminopropane; (b) coupling 2-N,N-dimethylaminomethyl-1,3-di-

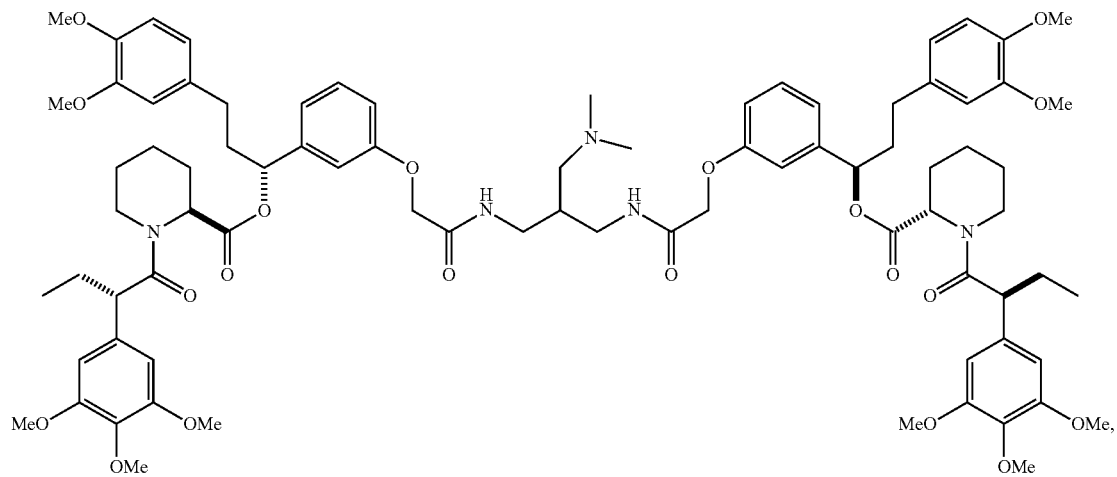

the method including coupling the dimeric alcohol, AP20793, with the carboxylic acid, AP20792, having the formula:

aminopropane with AP20792 to produce the dimeric alcohol, AP20793; and (c) coupling the AP20793 so produced with AP17362 to yield AP20187. In particular embodiments, the method further includes the step of producing AP17362 by coupling AP17360 with methyl-L-pipecolic acid, or a salt thereof.

In any of the above methods, the method can further include recovering the compound so produced, or a salt thereof, from the reaction mixture.

In any of the above methods, the method can include activating an acid with an activating agent selected from DCC, DIPCDI, DIEA, BOP, PyBOP, HBTU, TBTU, HOBt and any other coupling reagents used in the preparation of coupling of carboxylic acids with alcohols or amines to form esters and amides, respectively, examples of which agents are disclosed herein. In any of the above methods, the reagents and/or products of the reaction may be substantially pure.

As used herein, the term "AP20187" refers to the compound depicted below and pharmaceutically acceptable salts thereof.

Other features and advantages of the invention will be apparent from the following detailed description and the claims.

DETAILED DESCRIPTION

We have discovered improved methods for synthesizing AP20187. These improvements contribute to the isomeric purity of the products, and to the overall efficiency and scalability of production. Of particular interest, as disclosed herein, one can avoid or reduce the level of impurities in the final product. Such impurities can frustrate even expensive and inconvenient purification procedures and can lead to a poorly performing reagent.

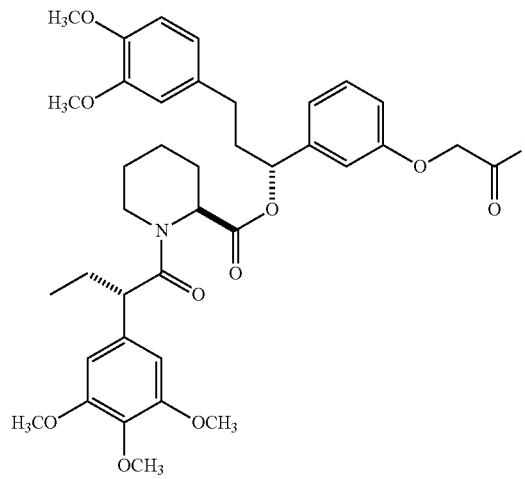
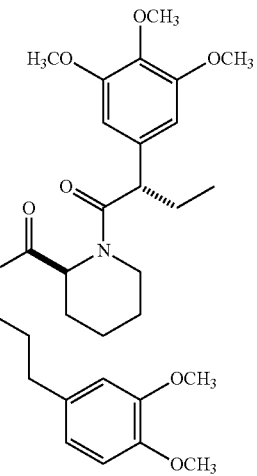

As used herein, the term "AP20793" refers to the compound depicted below and pharmaceutically acceptable salts thereof.

The "bottom half" of AP20187 is formed from AP17362. AP17362 is produced in high purity via steps 6-8 (see Examples 1f-1h). Some remaining

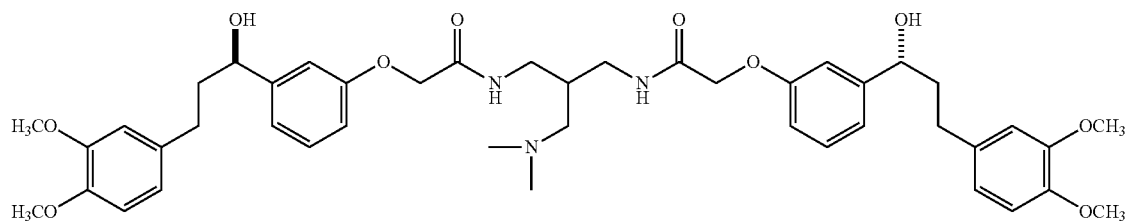 [SMILES: COc1ccc(CC[C@@H](O)c2cccc(OCC(=O)NCC(CNC(=O)COc3cccc([C@H](O)CCc4ccc(OC)c(OC)c4)c3)CN(C)C)c2)cc1OC]

As used herein, "substantially pure" refers to compositions containing a compound of interest, such as diastereomeric impurity, in which the compound of interest is present in the composition in a diastereomeric excess of from 50% to 100%, 60% to 99.9%, 75% to 99.9%, 50% to 99%, 50% to 98%, 80% to 100%, 90% to 100%, or from 94% to 99.8%. Substantially pure compositions can be prepared and analyzed using the chromatographic methods described herein. Substantially pure compositions can include non isomeric impurities (i.e., solvents, salts, and reaction side products).

impurities may readily be removed by crystallization of AP17362.

In an alternative synthetic approach, a chiral synthesis of AP17360 is utilized (as described in Example 3) to further reduce the introduction the isomeric impurity (R)-2-(3,4,5-Trimethoxyphenyl)butyric acid.

Coupling of N-acyl amino acids with alcohols via a DCC mediated intermediate (such as that used in step 9 (see Example 1i)) causes low levels of racemization to the alpha position of the carboxylic acid component (AP17362, carbon 2/2'). The extent of racemization is controlled by reaction conditions and results in the formation of AP20187 diastereomers.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

Example 1

Synthesis of AP20187

AP20187 was prepared using standard organic chemical synthetic methodology in a convergent multistep process.

(1a) Step 1. Synthesis of (E)-3-(3,4-Dimethoxyphenyl)-1-(3-hydroxyphenyl)-2-propen-1-one (AP14894)

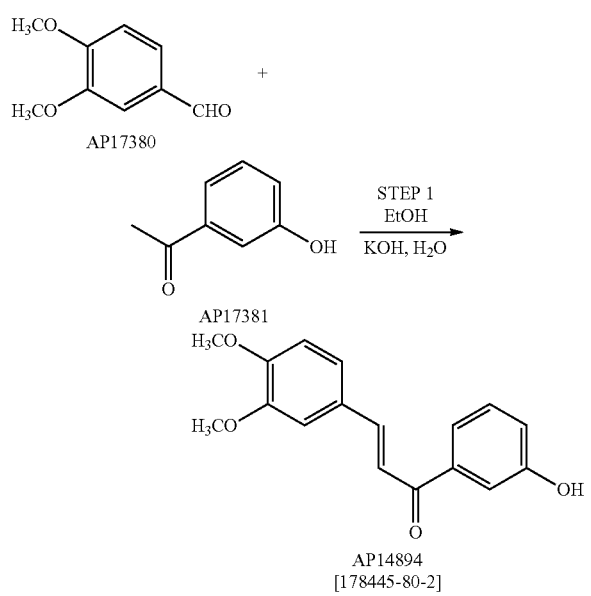

A solution of 3,4-dimethoxybenzaldehyde AP17380 (400 g, 2.41 moles) and 3'-hydroxyacetophenone AP17381 (328 g, 2.41 moles) in EtOH (3200 mL) was treated with a solution of aqueous KOH (536 g, 1200 mL) over a 1 hour period. The resulting solution was allowed to stir for 16 h at room temperature. The reaction mixture was then treated with EtOH (2000 mL) followed by water (1200 mL). A solution of EtOH/water (3400 mL, 1:1) was then added and the reaction mixture acidified to pH 6 using concentrated HCl (720 mL). After addition of acid, water (4000 mL) was added to induce precipitation. The resulting mixture was left stirring overnight and the solids then filtered, washed with water (2×900 mL) and then hexane (2×800 mL). The product was dried under vacuum for 3 hours and then placed in a vacuum oven at
50° C. for 6 days to provide AP14894 (609 g, 89%) as a yellow solid: mp 138-139° C.; TLC (EtOAc/hexane, 1:1) Rf=0.35; $^1$H NMR (DMSO-d$_6$, 300 MHz) 9.85 (br s, 1H), 7.71 (d, J=6.6 Hz, 2H), 7.61 (d, J=7.7 Hz, 1H), 7.53 (d, J=1.7 Hz, 1H), 7.47 (d, J=1.7 Hz, 1H), 7.39-7.34 (m, 2H), 7.07-7.00 (m, 2H), 3.87 (s, 3H), 3.82 (s, 3H); $^{13}$C NMR (DMSO-d$_6$, 75 MHz) 189.4, 158.2, 151.6, 149.4, 144.7, 139.7, 130.1, 127.9, 124.2, 120.4, 120.2, 119.7, 115.0, 112.0, 111.2, 56.1, 56.0; LRMS (ES+) (M+H)$^+$285; Anal. Calcd for C$_{17}$H$_{16}$O$_4$: C, 71.82; H, 5.67. Found: C, 71.55; H, 5.61.

(1b) Step 2. Synthesis of (3-(3,4-Dimethoxyphenyl)-1-(3-hydroxyphenyl)-1-propanone (AP14895)

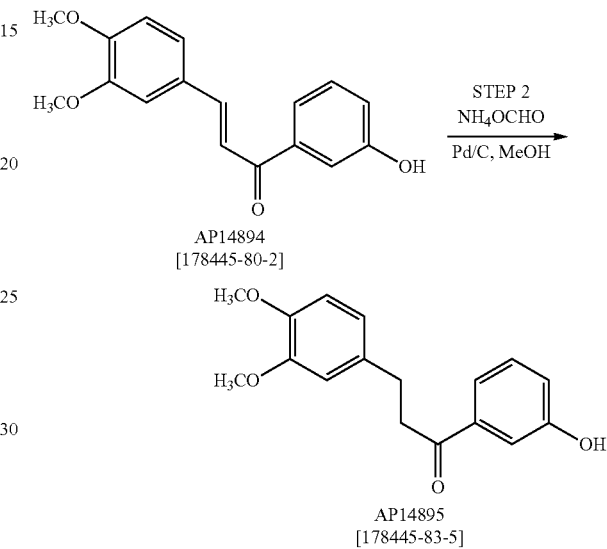

Pd/C (80.0 g, 5 wt %) was charged into a 5 L reactor containing MeOH (600 mL). Ammonium formate (132.4 g, 2.10 moles) was then charged into the reactor and magnetic agitation commenced. AP14894 (400 g, 1.41 moles) in MeOH (1000 mL) was then charged to the reactor. The reactor was equipped with a nitrogen purge and reflux condenser. The reaction mixture was heated at reflux (55° C.) for 3.5 hours after which time TLC analysis indicated all starting material had been consumed. The reaction mixture was then filtered and the filter cake washed with hot MeOH (1100 mL). The filtrate was then heated to 50° C. and water (2750 mL) added. The resulting solid precipitate was agitated overnight and the solids then collected by filtration, washed with water (1100 mL), and air dried for 7 hours. The solids were then placed in a vacuum oven at 70° C. for 3 days. Product, AP14895, (344.5 g, 86%) was obtained as an off-white solid: mp 132-134° C.; TLC (EtOAc/hexane, 1:1) Rf=0.42; $^1$H NMR (DMSO-d$_6$, 300 MHz) 9.73 (s, 1H), 7.43 (d, J=7.8 Hz, 1H), 7.33-7.28 (m, 2H), 7.02 (dd, J=8.0, 1.9 Hz, 1H), 6.88-6.74 (m, 3H), 3.73 (s, 3H), 3.70 (s, 3H), 3.20 (t, J=7.4 Hz, 2H), 2.86 (t, J=7.5 Hz, 2H); $^{13}$C NMR (DMSO-d$_6$, 75 MHz) 199.6, 158.0, 149.0, 147.5, 138.5, 134.1, 130.1, 120.5, 119.3, 114.5, 112.9, 112.3, 55.9, 55.8, 40.2, 29.6; LRMS (ES+) (M+NH4)$^+$304; Anal. Calcd for C$_{17}$H$_{18}$O$_4$: C, 71.31; H, 6.34. Found: C, 71.28; H, 6.21.

(1c) Step 3. Synthesis of [3[3-(3,4-dimethoxyphenyl)-1-oxopropyl]phenoxy]-acetic acid,1,1-dimethylethyl ester (AP14896)

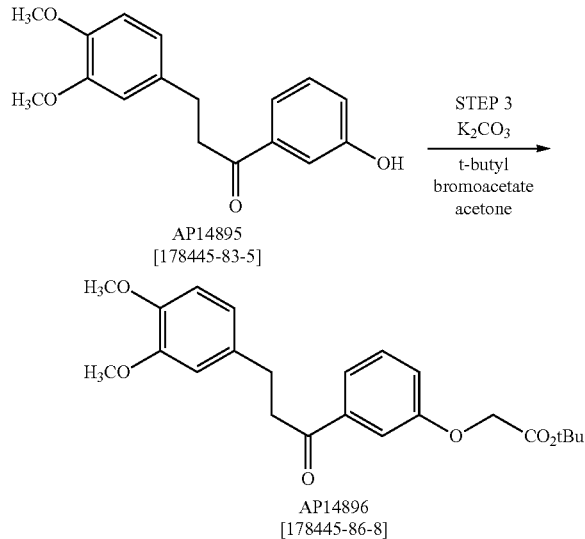

A solution of AP14895 (458 g 1.60 moles) in acetone (4580 mL) was treated with K₂CO₃ (332 g) followed by the dropwise addition of a solution of tert-butyl bromoacetate (258.3 mL, 1.60 moles) in acetone (338 mL) over a 1 hour period. The reaction mixture was heated at reflux for 2 hours and then allowed to stir at room temperature overnight. The reaction mixture was shown to be ~50% complete by TLC analysis and so was further heated at reflux for an additional 16 hours. After this time the reaction mixture was filtered, the filtercake washed with hot acetone (600 mL), the filtrate concentrated on a rotary evaporator, and then dissolved in MeOH (2500 mL). The methanolic solution was heated to boil and water (500 mL) added till the solution becomes cloudy. The solution was reheated to boil and allowed to cool to room temperature. The resulting precipitate was filtered, dried under vacuum for 2 hours, washed with hexane (600 mL), and placed in a vacuum oven at 40° C. overnight.

The crude product (439 g) was recrystallized by dissolving in MeOH (2175 mL), heating to reflux, and adding water till a cloudy point was observed. Reheating the solution to boil, followed by slow cooling, results in a precipitate which was filtered, dried under vacuum for 2 hours, and was placed in a vacuum oven at 40° C. overnight. Product, AP14896, (390 g, 75%) was obtained: mp 58-58.5° C.; TLC (EtOAc/hexane, 1:1) Rf=0.65; IR (neat) 2975, 1750, 1685, 1590, 1515, 1445, 1370, 1260, 1235, 1155, 1080, 1030 cm-1; $^1$H NMR (CDCl$_3$, 300 MHz) 7.57 (d, J=7.7 Hz, 1H), 7.47 (d, J=2.3 Hz, 1H), 7.39 (t, J=8.0 Hz, 1H), 7.12 (dd, J=8.0, 2.3 Hz, 1H), 6.82-6.77 (m, 3H), 4.56 (s, 2H), 3.87 (s, 3H), 3.85 (s, 3H), 3.25 (t, J=7.9 Hz, 2H), 3.00 (t, J=7.8 Hz, 2H), 1.49 (s, 9H); $^{13}$C NMR (CDCl$_3$, 75 MHz) 199.2, 168.0, 158.6, 149.4, 147.9, 138.7, 134.2, 130.1, 121.8, 120.6, 113.6, 112.3, 111.9, 83.0, 66.1, 56.4, 56.3, 41.1, 30.2, 28.4; LRMS (ES+): (M+NH4)$^+$418, (M+Na)$^+$423; Anal. Calcd for C$_{23}$H$_{28}$O$_6$: C, 68.98; H, 7.05. Found: C, 68.85; H, 7.07.

(1d) Step 4. Synthesis of [3[(1R)-3-(3,4-dimethoxyphenyl)-1-hydroxypropyl]phenoxy]-acetic acid (AP20792)

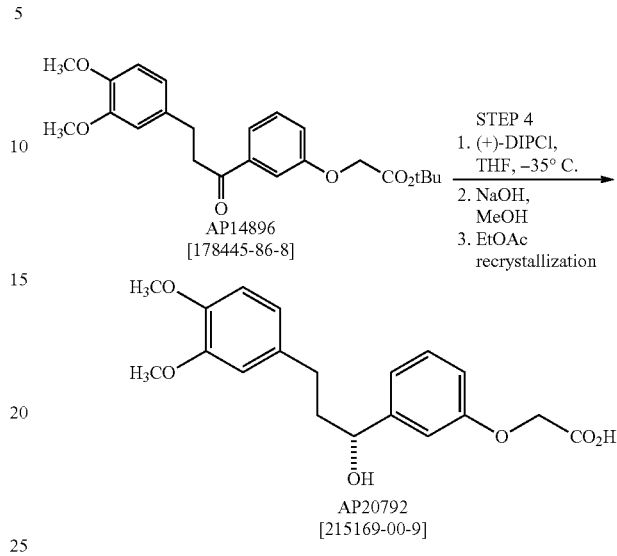

A solution of ketone AP14896 (200 g, 0.499 moles) in THF (1113 mL) under an atmosphere of nitrogen at −35° C. was treated with (+)-DIP-Chloride™ (220 g, 0.686 moles). The resulting mixture was allowed to stir at −25 to −35° C. for 6 hours, after which time the mixture was treated with water (260 mL) and concentrated on a rotary evaporator to remove THF. The concentrated mixture was then treated with MeOH (500 mL) followed by a 5N NaOH solution (400 mL) and the reaction stirred for 1 hour. Concentration of the reaction mixture to remove MeOH afforded an aqueous residue which was adjusted to pH 6 by the addition of a 2N HCl solution and allowed to stir for 16 hours after which time the mixture was washed with EtOAc (3×400 mL). The aqueous layer was further adjusted to pH 3 and the resultant precipitated solids stirred for 5 hours, filtered, and triturated with a 1% aqueous citric acid solution (200 mL). The solids were allowed to dry under vacuum for 2 hours and transferred to a vacuum oven and heated at 40° C. overnight to afford product, AP20792, (170 g, 98%) as a colorless solid.

The product was recrystallized in the following manner AP20792 (341.3 g) was suspended in EtOAc (900 mL) and heated at reflux for 2.5 hours with agitation and filtered while hot. The filtercake was weighed (6 g, ~1.8%). The filtrate was reheated to boil for 2 hours then seeded with material of 99.5% ee and the solution allowed to cool to room temperature with agitation. The solids were filtered and placed in a vacuum oven at 40° C. for 2 days to afford product (25 g, 74%) as a colorless solid: mp 125.5-126.5° C.; TLC (AcOH:MeOH:CHCl$_3$, 2:5:93) Rf=0.22; [α]$^{22}_D$+ 6.36 (c=1.00, DMSO); UV (MeOH) λmax 284 (ε2,712, sh), 278 (ε4,343), 272 (ε3,907, sh), 219 (ε14,081, sh) nm; $^1$H NMR (CD$_3$OD, 300 MHz) 7.02 (t, J=8.1 Hz, 1H), 6.74-6.71 (m, 2H), 6.63-6.48 (m, 4H), 4.42 (s, 2H), 4.35 (t, J=6.0 Hz, 1H), 3.57 (s, 3H), 3.56 (s, 3H), 2.46-2.28 (m, 2H), 1.85-1.67 (m, 2H); $^{13}$C NMR (CD$_3$OD, 75 MHz) 171.6, 158.5, 149.3, 147.6, 147.2, 135.3, 129.3, 120.6, 119.2, 113.3, 112.5, 112.4, 112.2, 73.1, 64.8, 55.5, 55.3, 41.0, 31.5; LRMS (ES+): (M+NH4)$^+$364, (M+Na)$^+$369; (ES−): M-345; HRMS (FAB): (M−H)-calcd: 345.1339, meas: 345.1335. Anal. Calcd for C$_{40}$H$_{48}$N$_2$O$_5$: C, 65.88; H, 6.40. Found: C, 65.70; H, 6.48.

(1e) Step 5. Synthesis of AP20793 from compound Y and AP20792

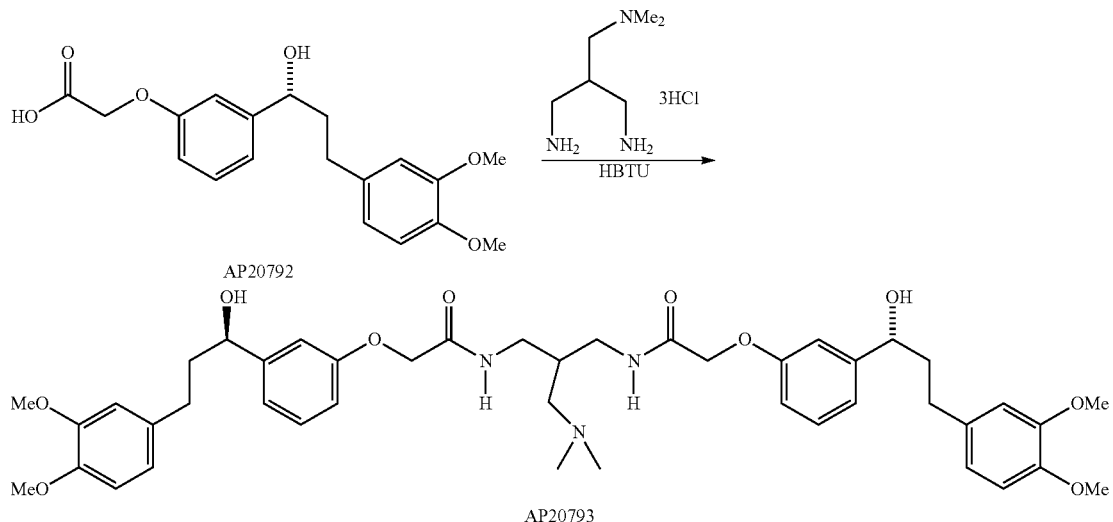

A stirred suspension of AP20792 (28 g, 0.081 mol), Compound Y.3HCl salt (see Examples 4 and 5) (9.6 g, 0.040 mol) and HBTU (31 g, 0.040 mol) in DMF (200 mL) was treated with triethylamine (70 mL) at room temperature. The reaction mixture was stirred for 1 hour, quenched with aqueous sodium carbonate, and extracted with AcOEt (3×300 mL). The organic solution was dried over $Na_2SO_4$, filtered, concentrated, and the crude material chromatographed on silica-gel, flushed with $CH_2Cl_2$:MeOH (100:5 to 20). Evaporation of the volatiles produced the product, AP20793, as a white foam (21 g, 66%). MS(M+1): 788.

(1f) Step 6. Synthesis of (R/S)-2-(3,4,5-Trimethoxyphenyl)butyric acid (AP14900)

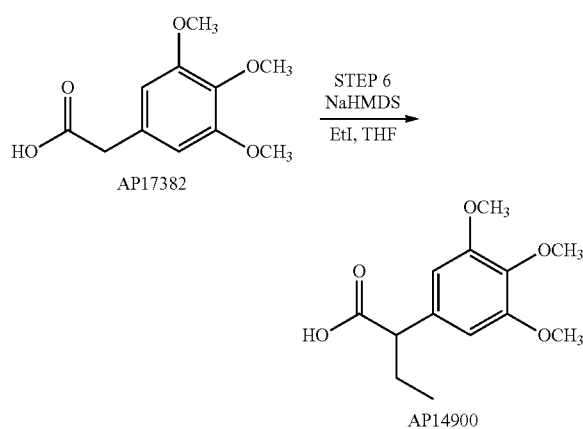

A 20 L reactor was purged with nitrogen and 3,4,5-trimethoxyphenylacetic acid (1000 g, 4.42 moles) added followed by THF (4000 mL). The suspension was stirred until all acid was dissolved. The resulting solution was then cooled to −25° C. and a 1.0 M THF solution of sodium bis(trimethylsilyl)amide added via cannula over a period of 1 hour in 2 batches of 500 mL each (10.0 moles total) and the mixture stirred for a further 30 minutes. The temperature of the reaction mixture was not allowed to rise above −15° C. during the course of addition. The resulting cream colored colloidal solution was treated at −25° C. with ethyl iodide (424 mL, 5.30 moles) via cannula over a 1 hour period. (A heat kick of ~5° C. may be observed for the initial addition of 50 mL of ethyl iodide. If this occurs, the temperature was adjusted to −25° C. and ethyl iodide addition continued.) The solution was allowed to stir at −25° C. for 2 hours as the colloidal solution slowly changes to a homogeneous brown solution. The brown solution was then allowed to warm to room temperature and stirred overnight. After this time the reaction mixture was quenched, with constant stirring, with water (1500 mL) and allowed to stir for a further 1.5 hours. The organic and aqueous layers were allowed to then separate and the organic layer removed and extracted with water (2×1000 mL). All aqueous solutions were combined and acidified to pH 2 by the addition of a 2N HCl solution (~3500 mL) and the solution extracted in batches of ~400 mL with an roughly equivalent volume of EtOAc (6000 mL total). The combined organic extracts were washed with brine (2×1500 mL) and reduced to a volume of ~2000 mL on a rotary evaporator at which time a brown crystalline solid began to precipitate. The solution was allowed to cool and the solid material was filtered, washed with a 1:1 EtOAc:hexanes solution, and the cream colored solids left in a vacuum oven at 40° C. overnight for a first crop of product, AP14900, (582.8 g). The filtrate was further evaporated and two additional crops (166.2 and 158.1 g) were obtained (907.05 g total, 80.6%).

(1g) Step 7. Synthesis of (S)-2-(3,4,5-Trimethoxyphenyl)butyric acid (AP17360)

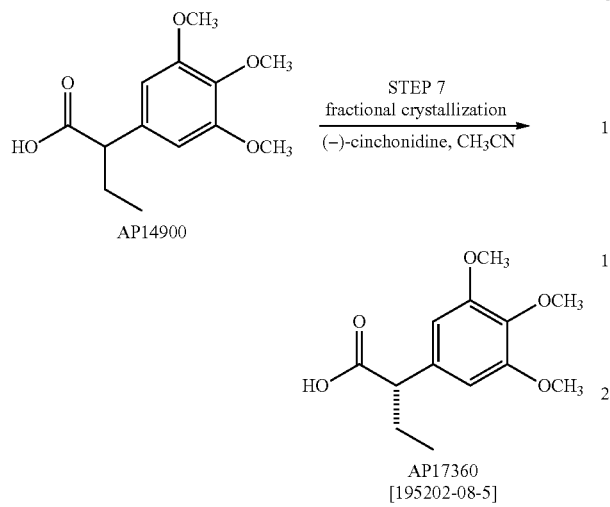

AP14900 (500 g, 1.97 moles) and (−)-cinchonidine (580 g, 1.97 moles) were charged into a 10 L reactor equipped with mechanical agitation. Acetonitrile (7500 mL) was added and the mixture heated to reflux for 30 minutes. The homogeneous solution was allowed to cool to room temperature with concomitant formation of salts. The solids were then filtered and the crystallization procedure was carried out an additional five times utilizing acetonitrile (7000, 7000, 6500, 6500, and 5000 mL) as solvent. The diastereomeric salt was then suspended in water (1400 mL) and dichloromethane (600 mL) and the solution was agitated until all salt was dissolved. The agitated mixture was adjusted to pH 2 by the addition of concentrated HCl, the organic layer was separated and the aqueous layer extracted with a further amount of $CH_2Cl_2$ (2×300 mL). The combined organic layers were then washed with a 1 N HCl solution (2×200 mL) to remove any remaining (−)-cinchonidine. These acid washings were then reextracted with $CH_2Cl_2$ (100 mL) and all $CH_2Cl_2$ solutions were combined. The combined organic solutions were washed with a 10% aqueous NaHCO3 solution (200 mL), dried over anhydrous MgSO4, concentrated on a rotary evaporator to a volume of ~250 mL, and then hexane was added (500 mL). The solution was heated and cooled and an additional portion of hexane (200 mL) was added. The solution was then concentrated on a rotary evaporator until solids appeared and was allowed to sit overnight. The resultant solids were filtered, triturated with hexane (2×300 mL), and placed in a vacuum oven at 50° C. for 84 hours to afford product (105.0 g, 21%) as an off-white solid: $[\alpha]^{22}_D$ +54.8 (c=1.07, MeOH, 30 min, 99.1% ee material); $^1$H NMR (DMSO-$d_6$, 300 MHz) 6.34 (s, 2H), 3.52 (s, 6H), 3.40 (s, 3H), 3.11 (t, J=7.6 Hz, 1H) 1.76-1.64 (m, 1H), 1.46-1.36 (m, 1H), 0.60 (t, J=7.3 Hz, 3H); $^{13}$C NMR (DMSO-$d_6$, 75 MHz) 175.1, 153.1, 136.9, 135.8, 105.4, 60.3, 56.2, 53.1, 26.7, 12.4. Anal. Calcd for $C_{13}H_{18}O_5$: C, 61.41; H, 7.13. Found: C, 61.47; H, 7.20.

(1h) Step 8. Synthesis of [S—(R*,R*)]-1-[1-oxo-2-(3,4,5-trimethoxyphenyl)butyl]-2-piperidinecarboxylic acid (AP17362)

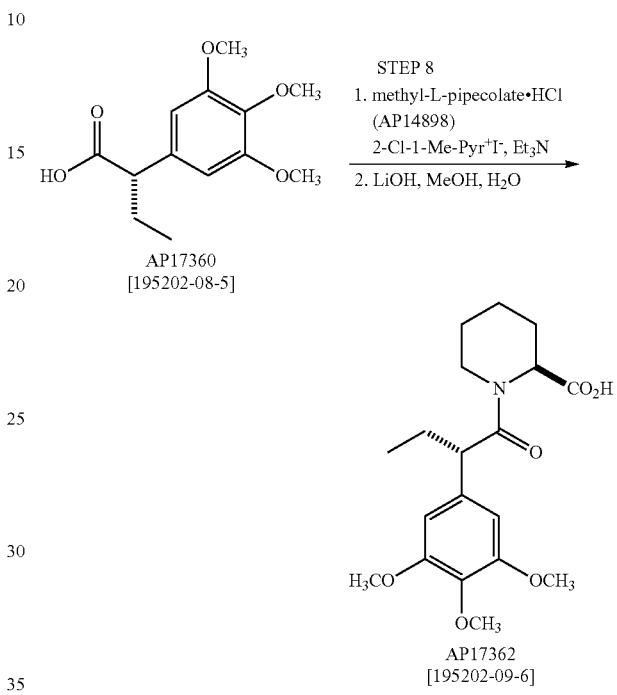

A solution of AP17360 (10.0 g, 0.039 moles) in $CH_2Cl_2$ (100 mL) was treated with methyl-L-pipecolate hydrochloride (7.2 g, 0.04 moles) followed by 2-chloro-1-methylpyridinium iodide (12.77 g, 0.050 moles). The reaction mixture was then treated dropwise with triethylamine (16.66 mL, 0.120 moles) resulting in a 22° C. rise in the temperature of the reaction mixture. The solution was allowed to stir for 2 hours, after which time the $CH_2Cl_2$ was removed on a rotary evaporator, the residue (~50 mL volume) was dissolved in MeOH (60 mL), and the solution was treated with water (5 mL) followed by lithium hydroxide monohydrate (8.26 g, 0.197 moles). The mixture was stirred overnight then treated with water (20 mL) and the MeOH removed on a rotary evaporator at 40° C. The resulting aqueous solution was treated with EtOAc (60 mL) followed by a saturated aqueous NaHCO3 solution (60 mL) and the organic layer washed with water (10 mL). The combined aqueous layers were then acidified to pH 4 by careful addition of a 2N HCl solution and the resulting suspension cooled to 10° C. The precipitate was filtered, triturated with a 1% aqueous citric acid solution (100 mL) and air dried under vacuum at 58° C. to provide product, AP17362, (10.5 g, 73%): mp 173.5-174° C.; $[\alpha]^2_D$ + 10.9 (c=1.01, DMSO, 30 min); UV (MeOH) λmax 270 (ε990), 232 (ε11,161), 207 (ε49,079) nm; $^1$H NMR (DMSO-$d_6$, 300 MHz) 6.55 (s, 2H), 5.13 (d, J=4.4 Hz, 1H), 3.85-3.64 (m, 11H), 2.77-2.70 (m, 1H), 2.12 (d, J=13.4 Hz, 1H), 1.99-1.85 (m, 1H), 1.65-1.55 (m, 4H), 1.38-1.18 (m, 2H), 0.84 (t, J=7.2 Hz, 3H); NMR (CD$_3$OD, 300 MHz) 6.74 (s, 2H), 5.43 (d, J=4.0 Hz, 1H), 4.13-3.83 (m, 11H), 3.03 (td, J=13.5, 3.0 Hz, 1H), 2.44 (d, J=13.8 Hz, 1H), 2.24-2.14 (m, 1H), 1.90-1.40 (m, 6H) 1.09 (t, J=7.3 Hz, 3H); $^{13}$C NMR (DMSO-d$_6$, 75 MHz) 172.9, 172.2, 153.0, 136.2, 105.4, 60.2, 56.2, 56.0, 51.8, 49.4, 43.1, 28.5, 26.8, 25.3, 21.0, 12.8; $^{13}$C NMR (CD$_3$OD, 75 MHz) 175.4, 174.5, 154.9, 137.5, 106.8, 61.5, 57.1, 53.9, 52.1, 45.2, 29.9, 28.2, 26.8, 22.3, 13.2; HRMS (FAB): (M–H)– calcd: 364.1760, meas: 364.1774. Anal. Calcd for C$_{19}$H$_{27}$O$_6$: C, 62.45; H, 7.45; N, 3.83. Found: C, 62.32; H, 7.61; N, 3.88.

(1i) Step 9. Synthesis of AP20187 from AP20793 and AP17362

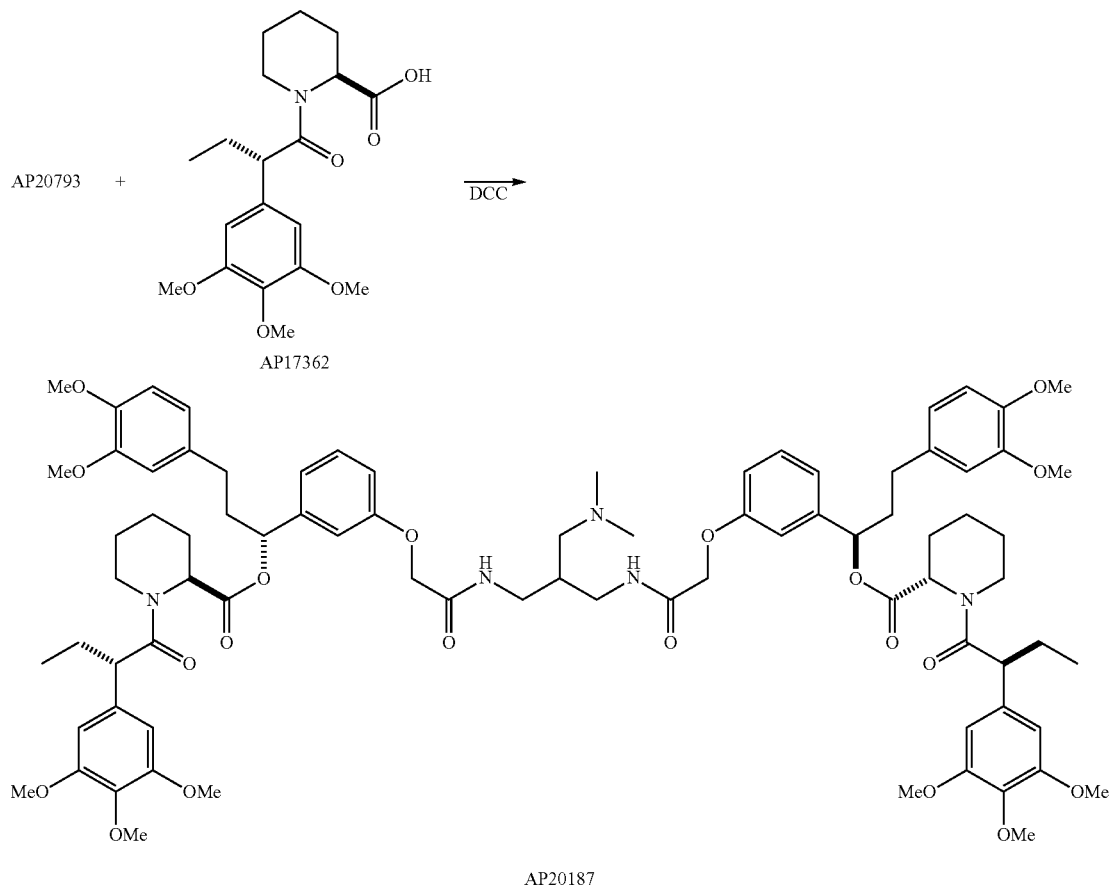

A mixture of AP20793 (19 g, 0.024 mol), AP17362 (19 g, 0.52 mol), and DMAP (5.6 g, 0.046 mol) in CH$_2$Cl$_2$ (60 mL) was treated with DCC (11 g, 0.053 mol) at 0° C. The reaction mixture was stirred for 2 hours at 0° C., and allowed to warm to room temperature with stirring for 48 hours. The mixture was filtered and then chromatographed on silica-gel to give pure product, AP20187, (6 g) and impure fractions (8 g). The yield of the pure product was 21 g, 59%.

(1j) Step 10. Synthesis of AP20187 mesylate salt

To a solution of AP20187 (30 g, 0.0202 mol) in AcOEt (150 mL) was added MeSO$_3$H (1.944 g, 0.0202 mol) in AcOEt (10 mL) at 0° C. over 10 minutes. After stirring at room temperature for 10 minutes, hexane (300 mL) was added and the resulting mixture was stirred at 0° C. for 4 hours. The white solid product was filtered and dried under vacuum (27 g, 85%).

Example 2

Chiral synthesis of (S)-2-(3,4,5-Trimethoxyphenyl)butyric acid (AP17360)

A chiral synthesis for AP17360 was developed to reduce the level of diastereomeric impurities present in AP1903 and AP20187.

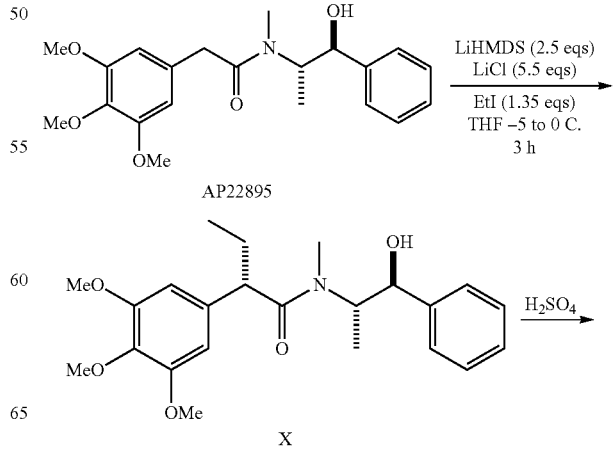

-continued

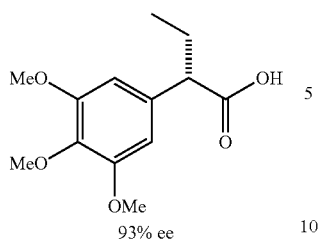

93% ee (3a) Synthesis of compound X

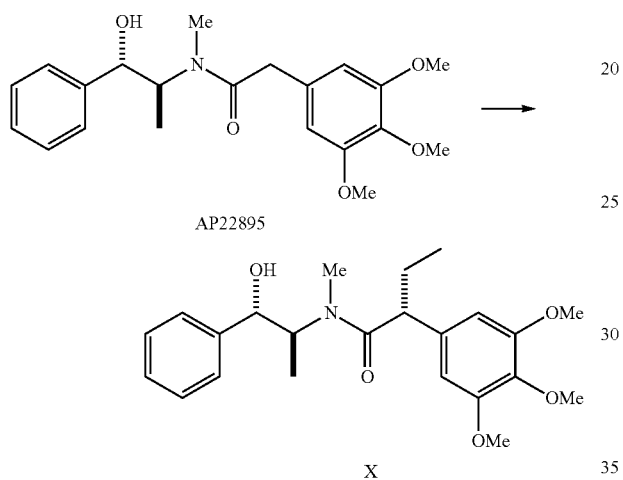

LiCl (3 g, 0.071 moles) was dried in a flask under high vacuum at 150° C. overnight. To this AP22895 (5 g, 0.013 moles) pre-dissolved in dry THF (135 mL) was added. The resulting mixture was cooled to −5° C. in an ice/salt bath and to this cooled mixture was added lithium bis(trimethylsilyl) amide (33 mL, 1.0 M in THF 0.033 moles). After stirring for 1 hour, ethyl iodide (5.5 mL 0.017 moles) was added dropwise. The reaction mixture was stirred at this temperature for an additional 3 hours. The mixture was then acidified with 2N HCl and extracted into EtOAc. The organic layer was dried over $MgSO_4$ and evaporated to produce a foamy material. The foamy material was taken up in diethylether and triturated with heptanes to furnish pure crystalline compound X (2.5 g).

(3b) Chiral synthesis of AP17360

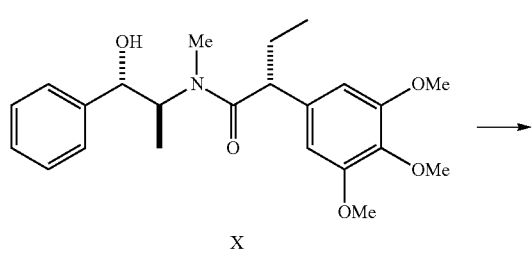

-continued

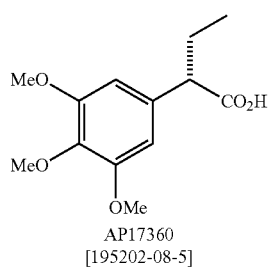

AP17360
[195202-08-5]

A solution of the amide (0.5 g, 0.0012 mol) in dioxane (6 mL) was slowly added to a cooled (0° C.) solution of 4.5 M $H_2SO_4$ (6 mL). When the addition was complete, the mixture was refluxed for 2 hours. The reaction was basified carefully with NaOH to pH 12, and washed with EtOAc twice. The combined organic layer was then dried and evaporated to recover the pseudoephedrine side product as an off white solid (0.17 g ca. 85% purity). The aqueous layer was then carefully acidified to pH 3 and extracted with EtOAc. Drying the organic layer over $MgSO_4$, filtration, and evaporation of the organic solvent afforded a crude material (0.33 g).

Example 4

Synthesis of 2-N,N-dimethylaminomethyl-1,3-diaminopropane trihydrochloride (compound Y)

The linker 2-N,N-dimethylaminomethyl-1,3-diaminopropane was synthesized for use as an intermediate in the synthesis of AP20187 as outlined in the synthetic scheme below.

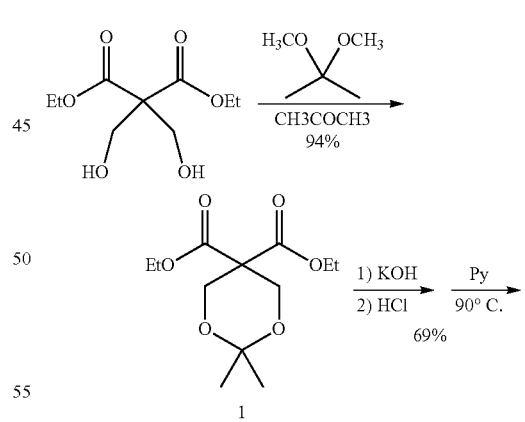

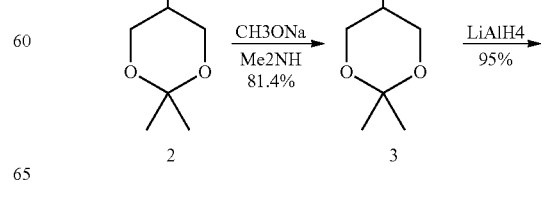

-continued

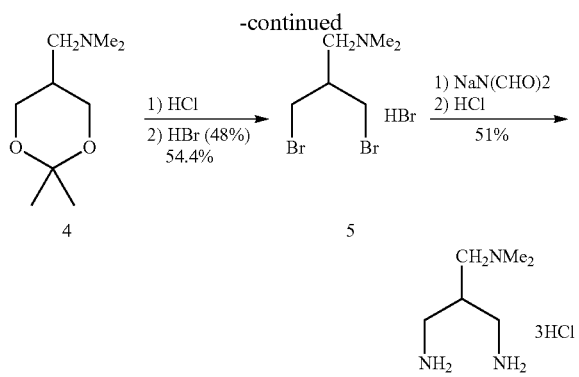

(4a) Synthesis of diethyl 2,2-dimethyl-1,3-dioxan-5,5-dicarboxylate (1)

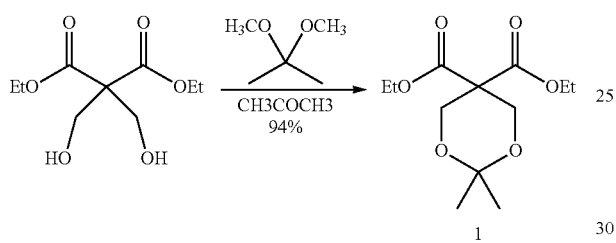

To a clear solution of diethyl bis(hydroxymethyl)malonate in 478 mL (6.52 mol) of acetone and 478 mL (8.45 mol) of acetone dimethylacetal was added 1.1 mL (42 mmol) of concentrated sulfuric acid and the reaction was stirred at room temperature overnight (19 hours). After 120 mL of saturated sodium carbonate was added, the mixture was stirred at room temperature for 15 minutes. The layers were separated and the semi-crystalline residue was washed with acetone (2×250 mL). The organics were evaporated. The residue was dispersed in 500 mL of ether and 250 mL of saturated $Na_2CO_3$, and stirred for 20 minutes. After the layers were separated, the organic layer was stirred with 250 mL of brine for 5 minutes and the layers separated. The organic layer was dried, evaporated, and placed under vacuum for 3 hours to produce a colorless oil, 527.5 g, in 94% yield.

(4b) Synthesis of diethyl 2,2-dimethyl-1,3-dioxan-5-carboxylate (2)

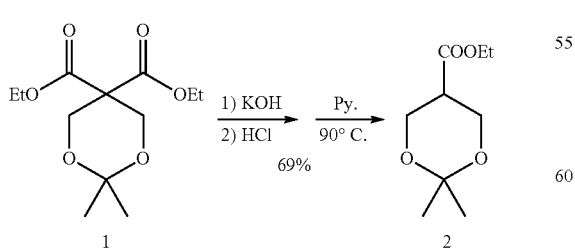

Potassium hydroxide (15 g, 2.667 mol) was stirred in 1843 mL of anhydrous ethanol and 97 mL of isopropanol to produce a clear solution. To this clear solution was added 1 (527 g, 2.026 mol) in 184 mL of ethanol and 10 mL of isopropanol. The reaction was stirred at room temperature under nitrogen for 5 hours and then evaporated. Water (580 mL) was added and cooled to −4° C. To this solution was added 58 mL of concentrated HCl and 1.2 L of 1.0 M HCl to reach a pH of 2.5 (followed by pH paper). The solution was extracted with ethyl acetate (4×1 L, pH adjusted to 2.5 following each extraction). The combined organics were dried and evaporated to a colorless oil. After the addition of 1.35 L of pyridine, the solution was stirred at 90° C. overnight (16 hours). The solution was distilled at 80° C. (ca. 150 mmHg) to remove the pyridine, and the product was removed by distillation at 55-65° C. (1-2 mmHg), 261.7 g, in 69% yield.

While diethyl bis(hydroxymethyl) malonate was used in step 4(a) to make the diethyl compound that was converted into compound 2, other aliphatic or aromatic malonate esters esters could also be used to generate the analogous aliphatic or aromatic ester of compound 2, which is subsequently converted into an amide and reduced as described below.

(4c) Synthesis of dimethylamino-2,2-dimethyl-1,3-dioxan-5-carboxylate (3)

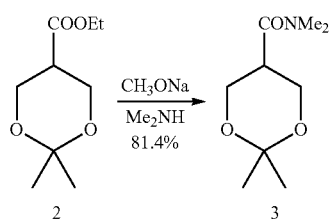

A mixture of 2 (210 g, 1.116 mol), 3.2 L of dimethylamine (2.0 M in THF, 4.6 mol), and 245 mL of sodium methoxide (25-30% in methanol) was stirred at room temperature under nitrogen overnight. After the addition of 300 g of ice to the flask, the mixture was heated at 40° C. to remove the excess dimethylamine (trapped in a solution of 1.0 M HCl over 2 hours), and then evaporated to 2/3 of the volume. The two layers were separated and the aqueous layer was extracted with $CH_2CL_2$ (2×400 mL). The organics were dried, evaporated, and co-evaporated with THF (2×300 mL) to give a light yellow solid, 170 g, in 81.4% yield.

(4d) Synthesis of 5-dimethylamino-2,2-dimethyl-1,3-dioxan (4)

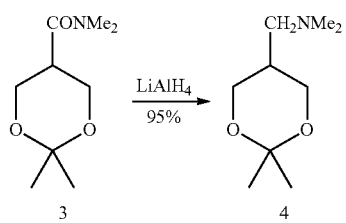

$LiALH_4$ (37.7 g) was suspended in 1.8 L of anhydrous THF under nitrogen at room temperature and stirred for 5 minutes. To this suspension was then dropped in a solution of 3 (169 g, 0.903 mol) in 1 L of anhydrous THF, keeping the inner temperature lower than 25° C. The mixture was refluxed for 4 hours. After cooling to room temperature, the reaction was quenched with 600 mL of pre-cooled water, keeping the inner temperature lower than 3° C. 1.5 L of CH$_2$CL$_2$ was added with stirring. The top clear solution was decanted. The remainder was placed into a separatory funnel, and the clear solution was drained slowly. The solid was washed with CH$_2$Cl$_2$ twice. The organics were washed with brine, dried, and evaporated to a light yellow oil, 149 g, in 95% yield.

(4e) Synthesis of 3-bromo-2-bromomethyl-N,N-dimethylpropylamine (5)

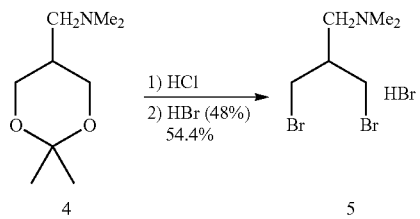

Compound 4 (60 g, 0.346 mol) was dissolved in 760 mL of THF and 673 mL of 1.0 M HCl. The reaction was stirred at room temperature overnight to finish the deprotection as judged by NMR. The mixture was evaporated at 55° C. to produce 65 g of oil. To the oil was added 500 mL of 48% HBr and the reaction was stirred at 150° C. overnight (21 hours). After cooling to room temperature, 250 mL of 48% HBr was added and the reaction mixture stirred for another 8 hours at 150° C. Another 350 mL of 48% HBr was added and the reaction mixture stirred again overnight at 150° C. The reaction mixture was cooled to room temperature, evaporated, and then co-evaporated with ethanol to produce a dark brown solid, which was refluxed in 650 mL of ethanol, filtered while hot, and cooled to room temperature forming crystals over several days. Filtration gave a light grey solid, 64 g, in 54.4% yield.

(4d) Synthesis of 2-N,N-dimethylaminomethyl-1,3-diaminopropane trihydrochloride (compound Y)

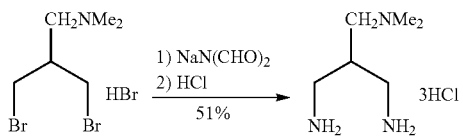

The dibromide salt 5 (58.5 g, 0.172 mol) was stirred in 410 mL of water and 540 mL of saturated Na$_2$CO$_3$ for 5 minutes and 1 L of CH$_2$Cl$_2$ was added. After stirring for another 5 minutes, the layers were separated. The aqueous layer was extracted with CH$_2$Cl$_2$ (4×600 mL). The organics were dried over Na$_2$CO$_3$ twice and evaporated to produce a solid (32 g). The solid was suspended in 1325 mL of anhydrous acetonitrile and sodium diformylamine (24.53 g, 0.258 mol) was added. The reaction was stirred at 100° C. overnight. After cooling to room temperature, the solid was filtered out and the filtrate was evaporated. The residue was dissolved in 630 mL of anhydrous ethanol and HCl in dioxane (4.0 M, 255 mL, 1.012 mol) was added. The reaction was stirred at 100° C. for 3 hours. After cooling to room temperature, the mixture was filtered. The solid was stirred in 320 mL of anhydrous ethanol overnight, filtered, and dried to give a white solid (compound Y), 21 g, in 51% yield.

Example 5

Synthesis of 2-N,N-dimethylaminomethyl-1,3-diaminopropane starting from 3-bromo-2-(bromomethyl)proprionic acid (5a) Synthesis of N,N-dimethyl-3-bromo-2-(bromomethyl) proprionic amide

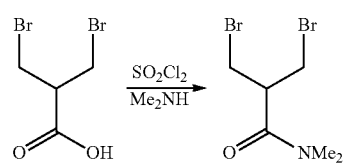

3-bromo-2-(bromomethyl)proprionic acid (50 g, 0.20 mol) was treated with SOCl$_2$ (40 mL, excess) at room temperature and the mixture refluxed for 1 hour. The excess SOCl$_2$ was evaporated and the residue dissolved in CH$_2$Cl) (200 mL).

To the above solution was added Me$_2$NH (250 mL, 2.0 M in methanol) at −40° C. over 20 minutes. The resulting reaction mixture was allowed to warm to −10° C. and was diluted with HCl (200 mL, 2.0 M). The mixture was extracted with CH$_2$Cl$_2$ (2×200 mL) and the combined organic fractions dried, filtered, and evaporated to produce a yellow oil (44 g, 79%).

(5b) Synthesis of 3-bromo-2-bromomethyl-N,N-dimethylpropylamine, quaternary salt form

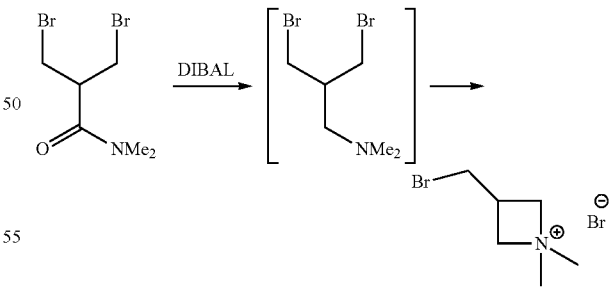

To a solution of N,N-dimethyl-3-bromo-2-(bromomethyl) proprionic amide (44 g) in CH$_2$Cl$_2$ (300 mL) was added DIBAL (450 mL, 1.0 M in toluene) at −40° C. over 30 minutes. The mixture was allowed to warm to −10° C. over 3 hours and the diluted with CH$_2$Cl$_2$ (1500 mL). The reaction was quenched with a mixture of water (300 mL) and methanol (100 mL) at −10° C., followed by stirring at a temperature less that 10° C. for 2 hours. The suspension was filtered, dried, and concentrated to ca. 300 mL. The product

25 crystallized upon standing overnight at room temperature. The crystals were separated from the solution and dried (19 g, 66%). MS(M+1): 178.

(5c) Synthesis of 2-N,N-dimethylaminomethyl-1,3-diaminopropane trihydrochloride (compound Y)

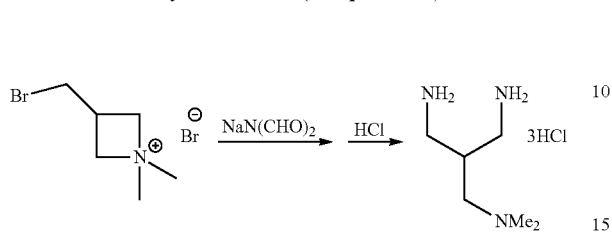

3-bromo-2-bromomethyl-N,N-dimethylpropylamine, quaternary salt form, was treated using the method described in Example 4d to produce 2-N,N-dimethylaminomethyl-1,3-diaminopropane.

OTHER EMBODIMENTS

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

This application claims benefit of and priority to U.S. Provisional Application No. 61/436,430, filed Jan. 26, 2011, which is incorporated by reference herein in its entirety.

Other embodiments are within the claims.

What is claimed is:

1. The compound

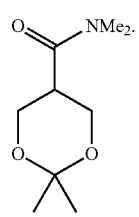

2. The compound

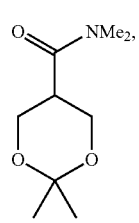

or a salt thereof.

26

3. The quaternary salt of 3-bromo-2-bromomethyl-N,N-dimethylpropylamine in solid form and described by the formula:

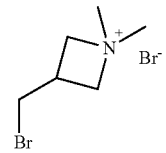

4. The compound AP22895, having the formula:

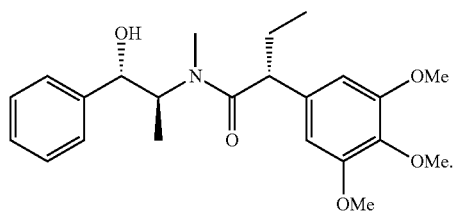 [SMILES: CC[C@@H](C(=O)N(C)[C@@H](C)[C@@H](O)c1ccccc1)c1cc(OC)c(OC)c(OC)c1]

5. A method for the chiral synthesis of the compound, AP17360, the method comprising: (a) reacting the compound AP22895 with ethyl iodide in the presence of a base to form compound X:

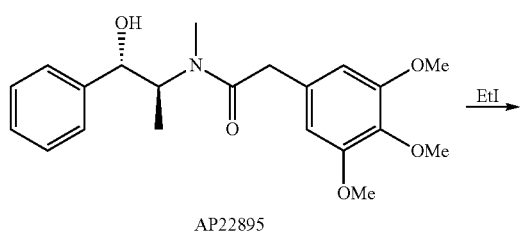

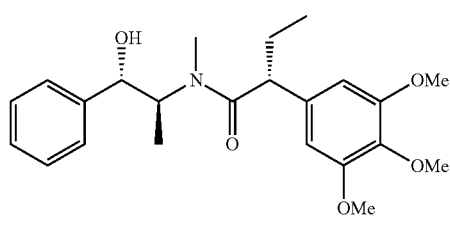

and (b) cleaving the compound X under acidic conditions to produce AP17360:

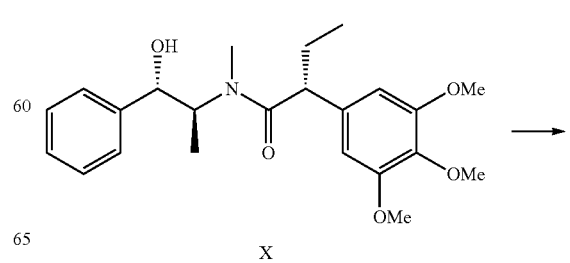

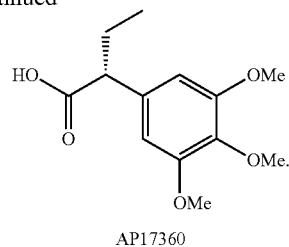

AP17360

6. The method of claim 5 wherein the base is lithium bis(trimethylsilyl)amide.

7. A method for producing dimethyl amide 3 by treating the corresponding ethyl ester with dimethylamine in the presence of base:

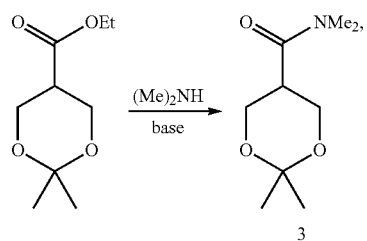

to form the desired dimethyl amide.

8. A method for producing compound 4 by providing the corresponding amide 3 and treating it with a reducing agent to produce compound 4:

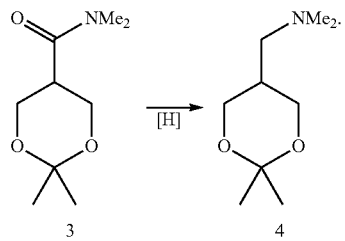

9. The method of claim 8 in which the reducing agent is LiAlH$_4$.

10. A method for producing 2-N,N-dimethylaminomethyl-1,3-diaminopropane (compound 6), the method comprising:

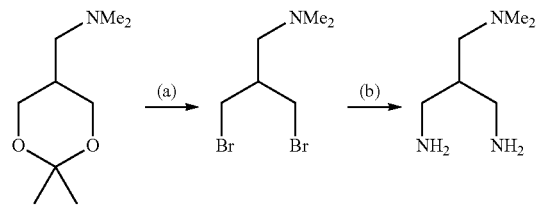

(a) reacting compound 4 with HBr to form 3-bromo-2-bromomethyl-N,N-dimethylpropylamine;
and
(b) reacting the 3-bromo-2-bromomethyl-N,N-dimethylpropylamine with diformylamine to produce 2-N,N-dimethylaminomethyl-1,3-diaminopropane.

11. A method for producing 2-N,N-dimethylaminomethyl-1,3-diaminopropane (compound 6), the method comprising providing the quaternary salt:

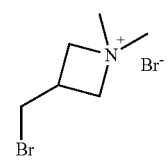

and reacting it with diformylamine to produce 2-N,N-dimethylaminomethyl-1,3-diaminopropane.

12. A method for producing AP20793:

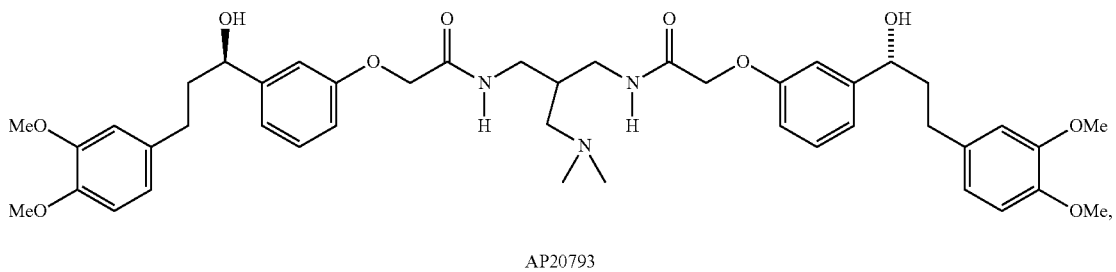 [SMILES: COc1ccc(CC[C@@H](O)c2cccc(OCC(=O)NCC(CNC(=O)COc3cccc([C@H](O)CCc4ccc(OC)c(OC)c4)c3)CN(C)C)c2)cc1OC]

AP20793 the method comprising: (a) dissolving a composition comprising the carboxylic acid, AP20792, of the formula:

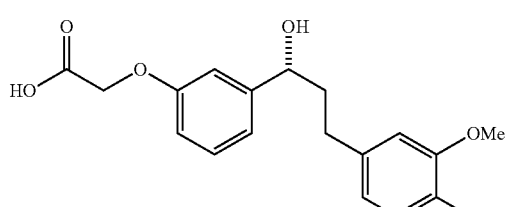

AP20792 in a solvent; (b) treating the resulting solution with a carboxyl activating agent to form activated AP20792; and (c) reacting the activated AP20792 with a composition comprising 2-N,N-dimethylaminomethyl-1,3-diaminopropane to form a mixture comprising AP20793.

13. The method of claim 12 which further comprises the step of producing 2-N,N-dimethylaminomethyl-1,3-diaminopropane by the method of claim 10.

14. The method of claim 12 which further comprises the step of producing 2-N,N-dimethylaminomethyl-1,3-diaminopropane by the method of claim 11.

15. A method for producing AP20187, having the formula:

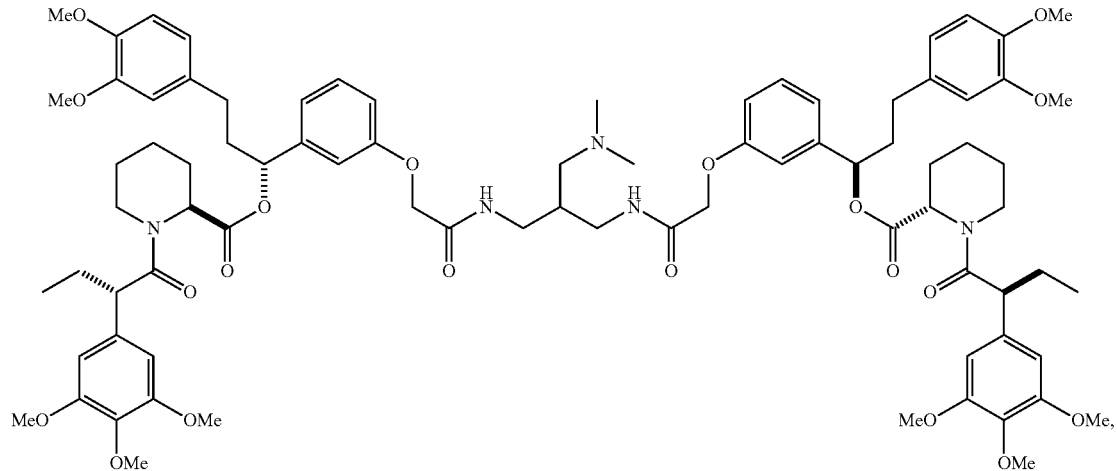

the method comprising coupling the dimeric alcohol, AP20793, with the carboxylic acid, AP20792, having the formula:

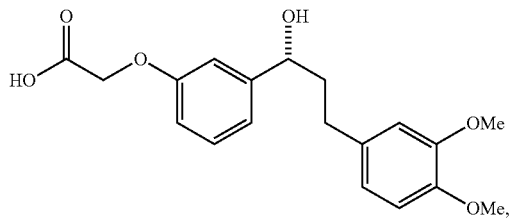 [SMILES: COc1ccc(CC[C@@H](O)c2cccc(OCC(=O)O)c2)cc1OC]

to yield AP20187.

16. A method for producing AP20187 by:
(a) coupling 2-N,N-dimethylaminomethyl-1,3-diaminopropane with AP20792 to produce the dimeric alcohol, AP20793; and
(b) coupling the AP20793 so produced with AP17362 to yield AP20187.

17. A method for producing AP20187 by:
(a) reacting 3-bromo-2-bromomethyl-N,N-dimethylpropylamine or the quaternary salt thereof with diformylamine to produce 2-N,N-dimethylaminomethyl-1,3-diaminopropane;
(b) coupling 2-N,N-dimethylaminomethyl-1,3-diaminopropane with AP20792 to produce the dimeric alcohol, AP20793; and
(c) coupling the AP20793 so produced with AP17362 to yield AP20187.

18. The method of claim 16 which further includes the step of producing AP17362 by coupling AP17360 with methyl-L-pipecolic acid, or a salt thereof.

19. The method of claim 17 which further includes the step of producing AP17362 by coupling AP17360 with methyl-L-pipecolic acid, or a salt thereof.

20. The method of any of claims 5-19 which further comprises recovering the compound so produced, or a salt thereof, from the reaction mixture.

* * * * *